United States Patent
Ohkubo et al.

(10) Patent No.: US 6,538,007 B1
(45) Date of Patent: Mar. 25, 2003

(54) N-[(R)-1-[3-(4-PIPERIDYL)PROPIONYL]-3-PIPERIDYLCARBONYL]-2(S)-ACETYLAMINO-β-ALANINE TRIHYDRATE, COMPOSITIONS THEREOF, AND METHODS FOR ITS USE

(75) Inventors: Mitsuru Ohkubo, Hyogo (JP); Satoru Kuroda, Osaka (JP); Hideko Nakamura, Osaka (JP); Hisashi Takasugi, Osaka (JP); Yosuke Fujii, Hyogo (JP); Keiichi Koga, Shiga (JP); Eiki Oikawa, Osaka (JP); Ryoki Orii, Osaka (JP); Shunsuke Goto, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/806,483

(22) PCT Filed: Oct. 7, 1999

(86) PCT No.: PCT/JP99/05520

§ 371 (c)(1),
(2), (4) Date: Apr. 12, 2001

(87) PCT Pub. No.: WO00/21932

PCT Pub. Date: Apr. 20, 2000

(30) Foreign Application Priority Data

Oct. 12, 1998 (AU) .............................................. PP6465

(51) Int. Cl.⁷ ..................... A61K 31/445; C07D 211/32
(52) U.S. Cl. ........................................ 514/316; 546/189
(58) Field of Search ........................... 546/189; 514/316

(56) References Cited

FOREIGN PATENT DOCUMENTS

| WO | WO 95/08536 |   | 3/1995 |
| WO | 96/29309 | * | 9/1996 |
| WO | WO 96/29309 |   | 9/1996 |
| WO | 97/33869 | * | 9/1997 |
| WO | WO 97/33869 |   | 9/1997 |

* cited by examiner

Primary Examiner—Alan L. Rotman
Assistant Examiner—Rita Desai
(74) Attorney, Agent, or Firm—Oblon, Spivak, McClelland, Maier & Neustadt, P.C.

(57) ABSTRACT

The trihydrates of β-alanine of the formula

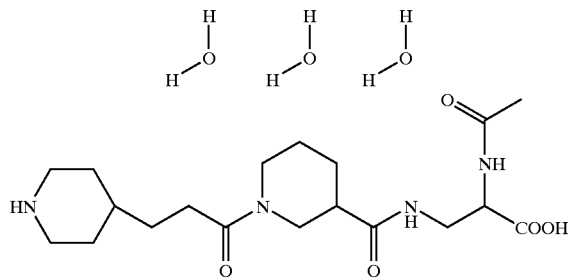

Are disclosed. Also method of antogonizing glycoprotein IIb/IIIa activity using these compounds is also disclosed.

13 Claims, No Drawings

N-[(R)-1-[3-(4-PIPERIDYL)PROPIONYL]-3-PIPERIDYLCARBONYL]-2(S)-ACETYLAMINO-β-ALANINE TRIHYDRATE, COMPOSITIONS THEREOF, AND METHODS FOR ITS USE the following formula [I] or [II] or a salt thereof, can be produced in a good yield.

The present invention provides a process for producing the β-Alanine derivative illustrated in the Processes 1 and 2 as shown below.

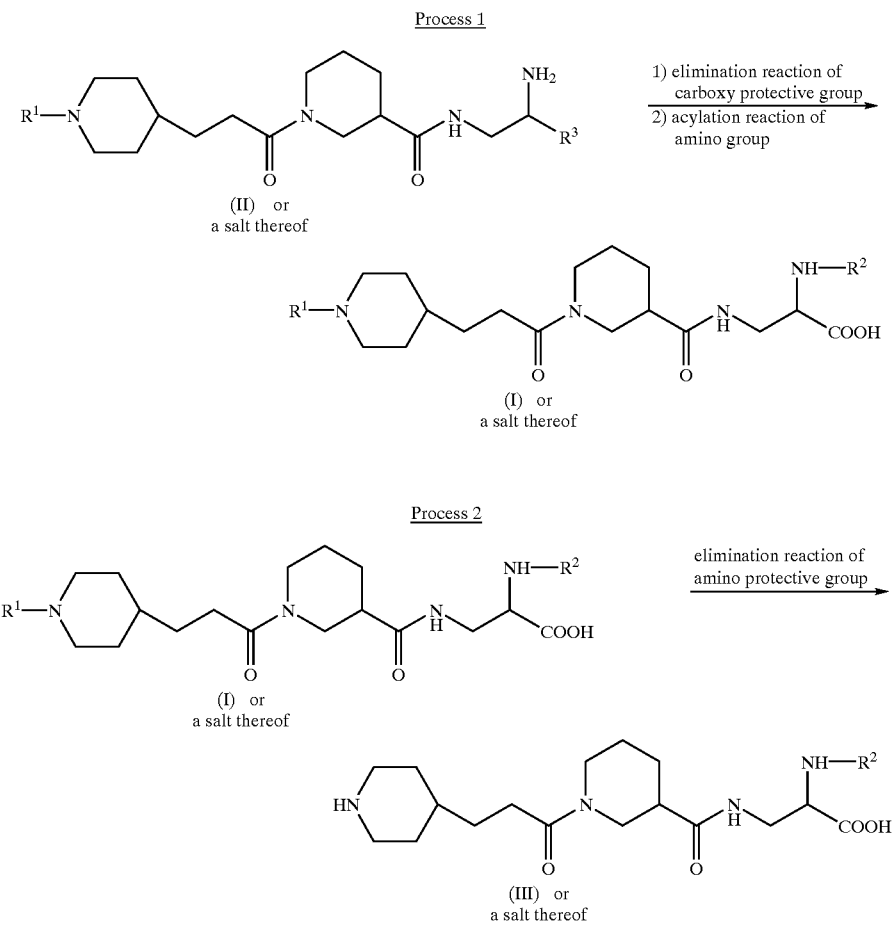

TECHNICAL FIELD

The present invention relates to processes for the preparation of β-alanine derivative. More particularly, it relates to processes for the preparation of β-alanine derivative which is glycoprotein IIb/IIIa antagonist, inhibitor of blood platelets aggregation and inhibitor of the binding of fibrinogen to blood platelets.

BACKGROUND ART

In PCT WO95/08536, the processes for producing β-alanine derivative which is useful as glycoprotein IIb/IIIa antagonist and inhibitor of platelet aggregation are disclosed.

DISCLOSURE OF INVENTION

The object of the present invention is to provide the producing process by which β-Alanine derivative, shown wherein
$R^1$ is amino protective group,
$R^2$ is acyl group, and
$R^3$ is protected carboxy.

Among the compounds (I), (II) and (III), some compounds are novel, and some are known. They can be prepared from the known compounds in a conventional manner in this field of the art or the similar manners to those disclosed in Preparations and/or Examples mentioned later in the present specification.

Suitable salts of the object compound (I) are conventional pharmaceutically acceptable and non-toxic salts, and include a metal salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N-dibenzylethylenediamine salt, etc.], an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, hydroiodide, sulfate, phosphate, etc.], a salt with an amino acid [e.g. arginine salt, aspartic acid salt, glutamic acid salt, etc.] and the like.

In the above and subsequent descriptions of this specification, suitable examples of the various definitions are explained in detail as follows:

The term "lower" is intended to mean 1 to 6 carbon atom(s), unless otherwise indicated.

The term "higher" is used to intend a group having 7 to 20 carbon atoms, unless otherwise provided.

The preferable number of the "one or more" in the term "one or more suitable substituent(s)" may be 1 to 3.

Suitable "protected carboxy" may be carboxy protected by a conventional protecting group such as an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, isopentyl ester, hexyl ester, isohexyl ester, 1-cyclopropylethyl ester, etc.] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxyethyl ester, 2-propionyloxyethyl ester, hexanoyloxymethyl ester, etc.], lower-alkanesulfonyl(lower)alkyl ester [e.g. 2-mesylethyl ester, etc.] or mono(or di or tri)halo(lower)alkyl ester [e.g. 2-iodoethyl ester, 2,2,2-trichloroethyl ester, etc.];

higher alkyl ester [e.g. heptyl ester, octyl ester, 3,5-dimethyloctyl ester, 3,7-dimethyloctyl ester, nonyl ester, decyl ester, undecyl ester, dodecyl ester, tridecyl ester, tetradecyl ester, pentadecyl ester, hexadecyl ester, heptadecyl ester, octadecyl ester, nonadecyl ester, adamantyl ester, etc.];

lower alkenyl ester [e.g. ($C_2$–$C_6$)alkenyl ester (e.g. vinyl ester, allyl ester, etc.)];

lower alkynyl ester [e.g. ($C_2$–$C_6$)alkynyl ester (e.g. ethynyl ester, propynyl ester, etc.)];

ar(lower)alkyl ester which may have one or more suitable substituent(s) [e.g. phenyl(lower)alkyl ester which may have 1 to 4 lower alkoxy, halogen, nitro, hydroxy, lower alkyl, phenyl, or halo(lower)alkyl, (e.g. benzyl ester, 4-methoxybenzyl ester, 4-chlorobenzyl ester, 4-nitrobenzyl ester, phenethyl ester, trityl ester, benzhydryl ester, bis(nethoxyphenyl)methyl ester, 3,4-dimethoxybenzyl ester, 4-hydroxy-3,5-di-tert-butylbenzyl ester, 4-trifluoromethylbenzyl ester, etc.)];

aryl ester which may have one or more suitable substituent(s) [e.g. phenyl ester which may have 1 to 4 lower alkyl, or halogen, (e.g. phenyl ester, 4-chlorophenyl ester, tolyl ester, 4-tert-butylphenyl ester, xylyl ester, mesityl ester, cumenyl ester, etc.), indanyl ester, etc.];

cycloalkyloxycarbonyloxy(lower)alkyl ester which may have lower alkyl (e.g., cyclopentyloxycarbonyloxymethyl ester, cyclohexyloxycarbonyloxymethyl ester, cycloheptyloxycarbonyloxymethyl ester, 1-methylcyclohexyloxycarbonyloxymethyl ester, 1-(or 2-)[cyclopentyloxycarbonyloxy]ethyl ester, 1-(or 2-)[cyclohexyloxycarbonyloxy]ethyl ester, 1-(or 2-)[cycloheptyloxycarbonyloxy]ethyl ester, etc.) etc.];

(5-(lower)alkyl-2-oxo-1,3-dioxol-4-yl)(lower)alkyl ester [e.g., (5-methyl-2-oxo-1,3-dioxol-4-yl)methyl ester, (5-ethyl 2-oxo-1,3-dioxol-4-yl)methyl ester, (5-propyl-2-oxo-1,3-dioxol-4-yl)methyl ester, 1-(or 2-)(5-methyl-2-oxo-1,3-dioxol-4-yl)ethyl ester, 1-(or 2-)(5-ethyl-2-oxo-1,3-dioxol-4-yl)ethyl ester, 1-(or 2-)(5-propyl-2-oxo-1,3-dioxol-4-yl)ethyl ester, etc.]; or the like.

Among them, the preferred one may be lower alkyl ester, ar(lower)alkyl ester, aryl ester which may have one or more suitable substituent(s), cycloalkyloxycarbonyloxy(lower)alkyl ester or lower alkanoyloxy(lower)alkyl ester, and the more preferred one may be methyl ester, ethyl ester, butyl ester, pentyl ester, isopentyl ester, isohexyl ester, benzyl ester, phenethyl ester, phenyl ester, indanyl ester, pivaloyloxymethyl ester or 1-cyclohexyloxycarbonyloxyethyl ester.

Suitable "amino protective group" may include acyl group as explained below, a conventional protective group such as ar(lower)alkyl which may have 1 to 3 suitable substituent(s) (e.g. benzyl, phenethyl, 1-phenylethyl, benzhydryl, trityl, etc.), [5-(lower)alkyl-2-oxo-1,3-dioxol-4-yl](lower)alkyl [e.g. (5-methyl-2-oxo-1,3-dioxol-4-yl)methyl, etc.] or the like; and the like.

Suitable "acyl group" and "acyl" may include aliphatic acyl, aromatic acyl, arylaliphatic acyl and heterocyclic-aliphatic acyl derived from carboxylic acid, carbonic acid, carbamic acid, sulfonic acid, and the like.

Suitable example of said "acyl group" may be illustrated as follows:

aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g., methoxycarbonyl, ethoxycarbonyl, t-butoxycarbonyl, t-pentyloxycarbonyl, heptyloxycarbonyl, etc.);

lower or higher alkylsulfonyl (e.g., methylsulfonyl, ethylsulfonyl, etc.);

lower or higher alkoxysulfonyl (e.g., methoxysulfonyl, ethoxysulfonyl, etc.); or the like;

aromatic acyl such as aroyl (e.g., benzoyl, toluoyl, naphthoyl, etc.);

ar(lower)alkanoyl [e.g., phenyl($C_1$–$C_6$)alkanoyl (e.g., phenylacetyl, phenylpropanoyl, phenylbutanoyl, phenylisobutanoyl, phenylpentanoyl, phenylhexanoyl, etc.), naphthyl($C_1$–$C_6$)alkanoyl (e.g., naphthylacetyl, naphthylpropanoyl, naphthylbutanoyl, etc.), etc.];

ar(lower)alkenoyl [e.g., phenyl($C_3$–$C_6$)alkenoyl (e.g., phenylpropenoyl, phenylbutenoyl, phenylmethacryloyl, phenylpentenoyl, phenylhexenoyl, etc.), naphthyl($C_3$–$C_6$)alkenoyl (e.g., naphthylpropenoyl, naphthylbutenoyl, etc.), etc.);

ar(lower)alkoxycarbonyl [e.g., phenyl($C_1$–$C_6$) alkoxycarbonyl (e.g., benzyloxycarbonyl, etc.), etc.];

aryloxycarbonyl (e.g., phenoxycarbonyl, naphthyloxycarbonyl, etc.);

aryloxy(lower)alkanoyl (e.g., phenoxyacetyl, phenoxypropionyl, etc.);

arylcarbamoyl (e.g., phenylcarbamoyl, etc.);

arylthiocarbamoyl (e.g., phenylthiocarbamoyl, etc.);

arylglyoxyloyl (e.g., phenylglyoxyloyl, naphthylglyoxyloyl, etc.);

arylsulfonyl which may have 1 to 4 lower alkyl (e.g., phenylsulfonyl, p-tolylsulfonyl, etc.); or the like;

heterocyclic acyl such as heterocycliccarbonyl;

heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.);

heterocyclicglyoxyloyl; or the like; and the like.

Suitable "heterocyclic" moiety in the terms "heterocycliccarbonyl", "heterocyclic(lower)alkyl", "heterocyclic(lower)alkenoyl" and "heterocyclicglyoxyloyl" as mentioned above, and "heterocyclic group" mean saturated or unsaturated monocyclic or polycyclic heterocyclic group containing at least one hetero-atom such as an oxygen, sulfur, nitrogen atom and the like. Among them, the preferable heterocyclic group may be heterocyclic group such as

- unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1-H-tetrazolyl, 2H-tetrazolyl, etc.), etc.;
- saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;
- unsaturated condensed heterocyclic group containing 1 to 4 nitrogen atom(s), for example, indolyl, isoindolyl, indolinyl, indolizinyl, benzimidazolyl, quinolyl, dihydroquinolyl, isoquinolyl, indazolyl, quinoxalinyl, dihydroquinoxalinyl, benzotriazolyl, etc.;
- unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;
- saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;
- unsaturated condensed heterocyclic group containing 1 to 2 oxygen atom(s) and 1 to 3 nitrogen atom(s), for example, benzoxazolyl, benzoxadiazolyl, etc.;
- unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;
- saturated 3 to 8-membered (more preferably 5 or 6-membered) heteromonocyclic group containing 1 to 2 sulfur atom(s) and 1 to 3 nitrogen atom(s), for example, thiazolidinyl, etc.;
- unsaturated 3 to 8-membered (more preferably 5 or 6-membered) heteromonocyclic group containing 1 to 2 sulfur atom(s), for example, thienyl, dihydrodithiinyl, dihydrodithionyl, etc.;
- unsaturated condensed heterocyclic group containing 1 to 2 sulfur atom(s) and 1 to 3 nitrogen atom(s), for example, benzothiazolyl, benzothiadiazolyl, etc.;
- unsaturated 3 to 8-membered (more preferably 5 or 6-membered) heteromonocyclic group containing an oxygen atom, for example, furyl, etc.;
- unsaturated 3 to 8-membered (more preferably 5 or 6-membered) heteromonocyclic group containing an oxygen atom and 1 to 2 sulfur atom(s), for example, dihydrooxathiinyl, etc.;
- unsaturated condensed heterocyclic group containing 1 to 2 sulfur atom(s), for example, benzothienyl, benzodithiinyl, etc.;
- unsaturated condensed heterocyclic group containing an oxygen atom and 1 to 2 sulfur atom(s), for example, benzoxathiinyl, etc.; and the like.

The acyl moiety as mentioned above may have one to ten, same or different, suitable substituent(s) such as lower alkyl (e.g., methyl, ethyl, propyl, etc.);

lower alkoxy (e.g., methoxy, ethoxy, propoxy, etc.);

lower alkylthio (e.g., methylthio, ethylthio, etc.);

lower alkylamino (e.g., methylamino, ethylamino, propylamino, etc.);

cyclo(lower)alkyl [e.g. cyclo($C_3$–$C_6$)alkyl (e.g. cyclopentyl, cyclohexyl, etc.]);

cyclo(lower)alkenyl [e.g. cyclo($C_3$–$C_6$)alkenyl (e.g., cyclohexenyl, cyclohexadienyl, etc.);

halogen (e.g., fluorine, chlorine, bromine, iodine); amino; amino protective group as mentioned above; hydroxy; protected hydroxy as mentioned below; cyano; nitro; carboxy; protected carboxy as mentioned above; sulfo; sulfamoyl; imino; oxo;

amino(lower)alkyl (e.g., aminomethyl, aminoethyl, etc.); carbamoyloxy; hydroxy(lower)alkyl (e.g., hydroxymethyl, 1 or 2-hydroxyethyl, 1 or 2 or 3-hydroxypropyl, etc.), or the like.

Suitable "protected hydroxy" may include acyl as mentioned above, phenyl(lower)alkyl which may have one or more suitable substituent(s) (e.g., benzyl, 4-methoxybenzyl, trityl, etc.), trisubstituted silyl [e.g., tri(lower)alkylsilyl (e.g., trimethylsilyl, t-butyldimethylsilyl, etc.), etc.], tetrahydropyranyl and the like.

The more preferred example of "amino protective group" may be lower alkoxycarbonyl or ar(lower)alkoxycarbonyl, and the most preferred one may be t-butoxycarbonyl or benzyloxycarbonyl.

Suitable "acyl group" of $R^2$ can be referred to aforementioned "acyl group". Among them, the more preferred one may be lower alkanoyl, and the most preferred one may be acetyl.

The processes of the present invention are explained in detail in the following.

Process 1

The object compound (I) or a salt thereof can be prepared by subjecting a compound (II) or a salt thereof to elimination reaction of carboxy protective group, and then the acylation reaction of amino group.

The Elimination Reaction of Carboxy Protective Group

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. lithium, sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like. Among them, the preferred one may be lithium anhydride.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.].

The elimination using Lewis acid such as trihaloacetic acid [e.g. trichloroacetic acid, trifluoroacetic acid, etc.] or the like, is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium, sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ulman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane tetrahydrofuran, etc., or a mixture thereof.

The reaction temperature of this reduction is not critical and the reaction is usually carried out under cooling to warming.

The Acylation Reaction of Amino Group

Suitable acylating agent to be used in the present acylation reaction may include the compound of the formula

$$R^2-OH \qquad (IV)$$

(wherein $R^2$ is acyl as mentioned before) or its reactive derivative, or a salt thereof.

Suitable reactive derivative at the amino group of the compound obtained by elimination reaction of carboxy protective group mentioned above may include Schiff's base type imino or its tautomeric enamine type isomer formed by the reaction of the compound obtained by elimination reaction of carboxy protective group mentioned above with a carbonyl compound such as aldehyde, ketone or the like; a silyl derivative formed by the reaction of the compound obtained by elimination reaction of carboxy protective group mentioned above with a silyl compound such as N,O-bis (trimethylsilyl)acetamide, N-trimethylsilylacetamide or the like; a derivative formed by the reaction of the compound obtained by elimination reaction of carboxy protective group mentioned above with phosphorus trichloride or phosgene, and the like.

Suitable reactive derivative of the compound (IV) may include an acid halide, an acid anhydride (e.g., acetic anhydride, etc.), an activated ester, and the like. Among them, the preferred one may be acid anhydride, and most preferred one may be acetic anhydride. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl $[(CH_3)_2{}^+N=CH-]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); and the like. These reactive derivatives can optionally be selected from them accordingly to the kind of the compound obtained by elimination reaction of carboxy protective group mentioned above to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely affect the reaction, or the mixture thereof.

When the compound obtained by elimination reaction of carboxy protective group mentioned above is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diisopropylcarbodiimide; N-ethyl-N'-(3-dimethylaminopropyl)carbodiimide; N,N-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may also be carried out in the presence of an organic or inorganic base such as an alkali metal, bicarbonate, tri(lower)alkylamine, pyridine, N-(lower) alkylmorphorine, N,N-di(lower)alkylbenzylamine, or the like.

The reaction temperature is not critical, and the reaction is usually carried out under cooling to heating.

Process 2

The object compound (III) or a salt thereof can be prepared by subjecting a compound (I) or a salt thereof to elimination reaction of the amino protective group.

This reaction can be carried out in a similar manner to that of Process 1 mentioned in the above, and therefore the reaction mode and reaction conditions [e.g. base, acid, catalyst, solvent, reaction temperature, etc.] of this reaction are to be referred to those as explained in Process 1.

When the object compound (III) thus obtained is in a salt form, it can be converted into a free form in a conventional manner (e.g., neutralization, column chromatography, recrystallization, desalting resin column chromatography, etc.).

The compounds obtained by the above Processes 1 and 2 can be isolated and purified by a conventional method such as pulverization, recrystallization, column-chromatography, reprecipitation or the like.

It is to be noted that each of the compounds (I), (II) and (III) may include one or more stereoisomer such as optical isomer(s) and geometrical isomer(s) due to asymmetric carbon atom(s) and double bond(s) and all such isomers and mixture thereof are included within the scope of this invention.

The compounds (I), (II) and (III) or a salt thereof include solvated compound [e.g., enclosure compound (e.g., hydrate, etc.)].

The compounds (I), (II) and (III) or a salt thereof include both its crystal form and non-crystal form.

The above invention would make it possible to produce β-alanine derivative in a good yield and/or to obtain a certain stereoisomer thereof which has a specific configuration in a good yield.

The compound (I) or a salt thereof is useful as an intermediate for preparing the compound (III) or a salt thereof.

So, the production of the compound (I) or a salt thereof in a good yield is useful as the effective production of the intermediate for the compound (III) or a salt thereof which is useful as glycoprotein IIb/IIIa antagonist or so.

The following Preparations and Examples are given for the purpose of illustrating the present invention in more detail.

Preparation 1

A mixture of 2(S)-benzyloxycarbonylamino-β-alanine (3.0 g) and p-toluenesulfonic acid monohydrate (2.88 g) in benzyl alcohol (15 ml) was heated to 120° C. in the flask fitted with Dean-Stark equipment. After dissolved, toluene (90 ml) was poured into it, and the mixture was refluxed for 3.5 hours. The mixture was cooled down to room temperature, and concentrated in vacuo. The residue was resolved in ethyl acetate, washed with saturated aqueous NaHCO$_3$, water and brine, dried over Na$_2$SO$_4$, and evaporated in vacuo. The product was resolved in ethyl acetate (50 ml), and cooled to 0° C. To the stirred solution, 4N—HCl in ethyl acetate (2.13 ml) was added dropwise at 0° C., then concentrated in vacuo. The oily product was solidified by addition of a mixture of ethyl acetate and isopropyl ether (1:1). The solid was washed with isopropyl ether, and dried in vacuo to give 2(S)-benzyloxycarbonylamino-β-alanine benzyl ester hydrochloride (2.75 g).

NMR (DMSO-d$_6$, δ): 3.04–3.29 (2H, m), 4.42–4.53 (1H, m), 5.02–5.17 (4H, m), 7.35 (5H, s), 7.37 (5H, s), 7.95 (1H, d, J=8.4 Hz)

MASS (m/z): 329 (M$^+$ free+1)

Preparation 2

To a suspension of 2(S)-benzyloxycarbonylamino-β-alanine (2.0 g) in a mixture of dioxane (14 ml), water (7 ml) and 1N aqueous NaOH (6.94 ml) was added di-tert-butyl dicarbonate (1.67 g) at 0° C. After 10 minutes, the temperature was allowed to reach to room temperature, and the mixture was stirred for 5 hours. The reaction mixture was evaporated in vacuo to remove dioxane, adjusted to pH 3.0 with aqueous 20% KHSO$_4$, then extracted with ethyl acetate. The organic layer was washed with water and brine, dried over Na$_2$SO$_4$, and evaporated in vacuo. The resulting solid was washed with diethyl ether to give N-tert-butoxycarbonyl-2(S)-benzyloxycarbonylamino-β-alanine (2.28 g).

NMR (CDCl$_3$, δ): 1.42 (9H, s), 3.44–3.67 (2H, m), 4.34–4.42 (1H, m), 5.13 (2H, s), 7.30–7.36 (5H, m)

Preparation 3

To a stirred solution of iodobenzene diacetate (7.26 g) in a mixture of ethyl acetate (44 ml), acetonitrile (44 ml) and water (22 ml) was added 2(R)-benzyloxycarbonylamino-succinamic acid (5.0 g) at ambient temperature. After stirred for 3 hours, the reaction mixture was cooled to 5° C., followed by stirring for 2 hours. Insoluble material was collected by filtration, washed with ethyl acetate, and dried under reduced pressure to give 2(R)-benzyloxycarbonylamino-β-alanine (4.15 g) as a white solid.

IR (KBr): 3303.5, 3027.7, 2948.6, 1693.2, 1656.5, 1623.8, 1592.9, 1542.8 cm$^{-1}$

NMR (D$_2$O-TFA, δ): 3.35 (1H, dd, J=13.4 and 8.7 Hz), 3.57 (1H, dd, J=13.4 and 5.3 Hz), 4.57 (1H, dd, J=8.7 and 5.3 Hz), 5.16 (2H, s), 7.43 (5H, s)

MASS (m/z): 239 (M+H)$^+$ mp: 238° C. (dec.)

$[\alpha]_D^{31}$: 8.6° (c=1.0, 1N NaOH aq.)

Preparation 4

Thionyl chloride (3.22 ml) was added dropwise to methanol (25 ml) at 4° C. under a nitrogen atmosphere. After stirred for 30 minutes, to the reaction mixture was added 2(R)-benzyloxycarbonylamino-β-alanine (3 g), followed by warming to the ambient temperature and stirring overnight. The insoluble material was collected by filtration, washed with diisopropyl ether, and dried under a reduced pressure to give 2(R)-benzyloxycarbonylamino-β-alanine methyl ester hydrochloride (3.15 g) as a white solid.

IR (KBr): 3365.2, 3317.0, 2950.5, 2885.0, 2850.3, 1733.7, 1695.1, 1594.8, 1537.0 cm$^{-1}$

NMR (DMSO-d$_6$, δ): 3.00–3.24 (2H, m), 3.68 (3H, s), 4.39–4.51 (1H, m), 5.07 (2H, s), 7.73 (5H, s), 7.94 (1H, d, J=8.2 Hz)

MASS (m/z): 253 (M+H)$^+$ mp: 166.0–166.5° C.

$[\alpha]_D^{30}$: 39.2° (c=1.0, MeOH)

The following compounds [Preparation 5 and 6] were obtained according to a similar manner to that of Preparation 4.

Preparation 5

2(R)-Benzyloxycarbonylamino-β-alanine ethyl ester hydrochloride

IR (KBr): 3322.7, 2863.8, 1727.9, 1695.1, 1596.8, 1540.8 cm$^{-1}$

NMR (DMSO-d$_6$, δ): 1.18 (3H, t, J=7.1 Hz), 3.06 (1H, dd, J=13.0 and 9.4 Hz), 3.22 (1H, dd, J=13.0 and 4.7 Hz), 4.13 (2H, q, J=7.1 Hz), 4.36–4.48 (1H, m), 5.08 (2H, s), 7.37 (5H, s), 7.94 (1H, d, J=8.2 Hz)

MASS (m/z): 267 (M+H)$^+$ mp: 141.0–141.5° C.

$[\alpha]_D^{30}$: 39.9° (c=1.0, MeOH)

Preparation 6

2(S)-Benzyloxycarbonylamino-β-alanine ethyl ester hydrochloride

IR (KBr): 3324.7, 2869.6, 1727.9, 1695.1, 1596.8, 1540.8 cm$^{-1}$

NMR (DMSO-d$_6$, δ) 1.18 (3H, t, J=7.1 Hz), 3.06 (1H, dd, J=13.0 and 9.4 Hz), 3.22 (1H, dd, J=13.0 and 4.7 Hz), 4.13 (2H, q, J=7.1 Hz), 4.36–4.48 (1H, m), 5.08 (2H, s), 7.37 (5H, s), 7.94 (1H, d, J=8.2 Hz)

MASS (m/z): 267 (M+H)$^+$ mp: 141.3–141.8° C.

$[\alpha]_D^{30}$: −39.1° (c=1.0, MeOH)

Preparation 7

To a mixture of (R)-1-[3-(1-tert-butoxycarbonyl-4-piperidyl)propionyl]-3-piperidinecarboxylic acid (20.0 g), 2(S)-benzyloxycarbonylamino-β-alanine methyl ester hydrochloride (17.2 g) and 1-hydroxybenzotriazole (8.07 g) in N,N-dimethylformamide (200 ml) was added dropwise 1-ethyl-3-(3-dimethylaminopropyl)carbodiimide (10.9 ml) at 0° C. The mixture was stirred at 4° C. for 15 hours, then poured into ice water (500 ml), and extracted with ethyl acetate (500 ml×2). The combined organic layer was successively washed with water, saturated aqueous NaHCO$_3$ and brine, dried over Na$_2$SO$_4$, and evaporated in vacuo. The residue was chromatographed on silica gel eluting with n-hexane-ethyl acetate (from 1:1 to ethyl acetate only) to give N-[(R)-1-[3-(1-tert-butoxycarbonyl-4-piperidyl)propionyl]-3-piperidylcarbonyl]-2(S)-benzyloxycarbonylamino-β-alanine methyl ester (30.5 g) as a colorless oil.

IR (KBr): 3307, 2933, 1724, 1689, 1535, 1434, 1365, 1272, 1243, 1164 cm$^{-1}$

NMR (CDCl$_3$, δ): 0.97–1.38 (2H, m), 1.46 (9H, s), 1.53–1.67 (7H, m), 2.27–2.67 (6H, m), 3.23–3.39 (3H, m), 3.69 (3H, s), 3.54–3.61 (1H, m), 4.07–4.14 (4H, m), 4.46–4.51 (1H, m), 5.12 (2H, s), 6.39–6.43 (1H, m), 7.32–7.35 (5H, m)

MASS (m/z): 503 (M−Boc+2)$^+$

The following compounds [Preparation 8 to 13] were obtained according to a similar manner to that of Preparation 7.

Preparation 8

N-[(S)-1-[3-(1-tert-Butoxycarbonyl-4-piperidyl)propionyl]-3-piperidylcarbonyl]-2(S)-benzyloxycarbonylamino-β-alanine methyl ester NMR (CDCl$_3$, δ): 0.98–1.84 (11H, m), 1.45 (9H, s), 2.30–2.38 (3H, m), 2.59–2.71 (2H, m), 3.32–4.10 (8H, m), 3.76 (3H, s), 4.40–4.50 (1H, m), 5.09 (1H, ABq, J=12.3 Hz), 5.13 (1H, ABq, J=12.3 Hz), 7.31–7.37 (5H, m)

MASS (m/z): 625 (M+Na)$^+$

Preparation 9

N-[(S)-1-[3-(1-tert-Butoxycarbonyl-4-piperidyl)propionyl]-3-piperidylcarbonyl]-2(R)-benzyloxycarbonylamino-β-alanine methyl ester NMR (CDCl$_3$, δ) 0.97–1.77 (11H, m), 1.46 (9H, s), 2.35–2.68 (5H, m), 3.27–4.21 (8H, m), 3.70 (3H, s), 4.47–4.53 (1H, m), 5.13 (2H, s), 7.32–7.38 (5H, m)

MASS (m/z): 625 (M+Na)$^+$

Preparation 10

N-[(R)-1-[3-(1-tert-Butoxycarbonyl-4-piperidyl)propionyl]-3-piperidylcarbonyl]-2(S)-benzyloxycarbonylamino-β-alanine benzyl ester IR (KBr): 1720, 1710, 1691, 1651 cm$^{-1}$ NMR (CDCl$_3$, δ): 0.92–1.15 (2H, m), 1.25–2.67 (15H, m), 1.46 (9H, s), 3.12–4.24 (7H, m), 4.46–4.58 (1H, m), 5.00–5.18 (4H, m), 6.40 (1H, d, J=9.3 Hz), 7.23–7.37 (10H, m)

MASS (m/z): 701 (M+Na)$^+$

Preparation 11

N-[(R)-1-[3-(1-tert-Butoxycarbonyl-4-piperidyl)propionyl]-3-piperidylcarbonyl]-2(S)-benzyloxycarbonylamino-β-alanine ethyl ester IR (KBr): 3309.2, 2977.5, 2935.1, 2859.9, 1726.0, 1689.3, 1652.7, 1535.1 cm$^{-1}$ NMR (DMSO-d$_6$, δ): 0.89–1.90 (11H, m), 1.18 (3H, t, J=7.1 Hz), 1.38 (9H, s), 2.20–2.80 (6H, m), 2.80–3.60 (3H, m), 3.65–4.45 (7H, m), 5.04 (2H, s), 7.31 (1H, dd, J=8.0 and 3.8 Hz), 7.95–8.10 (1H, m)

MASS (m/z): 639 (M+Na)$^+$

Preparation 12

N-[(R)-1-[3-(1-tert-Butoxycarbonyl-4-piperidyl)propionyl]-3-piperidylcarbonyl]-2(R)-benzyloxycarbonylamino-β-alanine methyl ester IR (KBr): 3309.2, 2935.1, 2859.9, 1726.0, 1689.3, 1535.1 cm$^{-1}$ NMR (DMSO-d$_6$, δ): 0.80–1.90 (11H, m), 1.38 (9H, s), 2.20–2.80 (6H, m), 2.80–4.00 (6H, m), 3.61 (3H, s), 4.10–4.45 (2H, m), 5.04 (2H, s), 7.36 (5H, s), 7.64 (1H, d, J=8.1 Hz), 7.95–8.15 (1H, m)

MASS (m/z): 603 (M+H)$^+$, 625 (M+Na)$^+$

Preparation 13

N-[(R)-1-[3-(1-tert-Butoxycarbonyl-4-piperidyl)propionyl]-3-piperidylcarbonyl]-2(R)-benzyloxycarbonylamino-β-alanine ethyl ester IR (KBr): 3309.2, 2977.5, 2935.1, 2859.9, 1726.0, 1689.3, 1654.6, 1533.1 cm$^{-1}$ NMR (DMSO-d$_6$, δ): 0.80–1.90 (11H, m), 1.17 (3H, t, J=7.1 Hz), 1.38 (9H, s), 2.20–2.80 (6H, m), 2.80–3.50 (3H, m), 3.65–4.45 (7H, m), 5.04 (2H, s), 7.36 (5H, s), 7.62 (1H, d, J=8.1 Hz), 7.95–8.10 (1H, m)

MASS (m/z): 617 (M+H)$^+$, 639 (M+Na)$^+$

Preparation 14

To a stirred solution of (R)-1-[3-(1-tert-butoxycarbonyl-4-piperidyl)propionyl]-3-piperidine carboxylic acid (1.0 g) in tetrahydrofuran (20 ml) was added dropwise isobutyl chloroformate (356 µl) and 4-methylmorpholine (300 µl) at −15° C. under a nitrogen atmosphere. To an ice cooled solution of 2(S)-benzyloxycarbonylamino-β-alanine methyl ester hydrochloride (783 mg) and N-(trimethylsilyl) acetamide (1.78 g) in tetrahydrofuran (30 ml) was added dropwise the above solution with stirring under a nitrogen atmosphere. The reaction mixture was allowed to warm to ambient temperature, and stirred for 2 hours, which was partitioned between ethyl acetate and water. The organic layer was separated, washed in turn with water, aqueous 5% KHSO$_4$, aqueous 5% NaHCO$_3$ and brine, and dried over MgSO$_4$. Evaporation of the solvent gave a residue, which was purified by silica-gel column chromatography eluting with n-hexane-ethyl acetate (from 1:6 to ethyl acetate only) to give N-[(R)-1-[3-(1-tert-butoxycarbonyl-4-piperidyl)propionyl]-3-piperidylcarbonyl]-2(S)-benzyloxycarbonylamino-β-alanine methyl ester (1.36 g) as a foam, which is the same compound obtained in Preparation 7.

Preparation 15

To a stirred solution of (R)-1-[3-(1-tert-butoxycarbonyl-4-piperidyl)propionyl]-3-piperidine carboxylic acid (1.0 g) and N,N-dimethylformamide (210 µl) in dichloromethane (10 ml) was added dropwise oxalyl chloride (240 µl) at 4° C. under a nitrogen atmosphere. To an ice cooled solution of 2(S)-benzyloxycarbonylamino-β-alanine methyl ester hydrochloride (940 mg) and N-(trimethylsilyl)-acetamide (2.85 g) in N,N-dimethylformamide (10 ml) was added dropwise the above solution with stirring under a nitrogen atmosphere. The reaction mixture was allowed to warm to ambient temperature, and stirred for 2 hours, which was partitioned between a mixture of ethyl-acetate and n-hexane and water. The organic layer was separated, washed in turn with water, aqueous 5% NaHCO$_3$ solution and brine, and dried over MgSO$_4$. Evaporation of the solvent gave a residue, which was purified by silica-gel column chromatography eluting with n-hexane-ethyl acetate (from 1:6 to ethyl acetate only) to give N-[(R)-1-[3-(1-tert-butoxycarbonyl-4-piperidyl)propionyl]-3-piperidylcarbonyl]-2(S)-benzyloxycarbonylamino-β-alanine methyl ester (0.89 g) as a foam, which is the same compound obtained in Preparation 15.

Preparation 16

To a solution of N-(t-butoxycarbonyl)-2(S)-benzyloxycarbonylamino-β-alanine (6.15 g) in methanol (120 ml) was added 10% Pd—C (50% wet, 1.2 g). The mixture was stirred vigorously, and hydrogen gas was bubbled for 1 hour. The catalyst was removed by filtration, and the filtrate was evaporated in vacuo. The residue was dissolved in tetrahydrofuran (70 ml) and cooled to 0° C. with ice bath. 1N NaOH (36 ml) was added, then acetic anhydride (3.77 ml) was added dropwise under stirring. The mixture was stirred for additional 1 hour at 0° C., then the pH of the mixture was adjusted to 2.5 with aqueous 20% KHSO$_4$. The resultant mixture was extracted with ethyl acetate-tetrahydrofuran (200 ml–100 ml) twice times. The combined organic layer was dried over Na$_2$SO$_4$ and evaporated in vacuo. The residue was recrystallized from diethyl ether to give N-(t-butoxycarbonyl)-2(S)-acetylamino-β-alanine (3.17 g).

IR (KBr): 3370, 3303, 1707, 1689, 1612, 1552, 1513, 1431, 1386, 1369, 1309, 1277, 1254, 1173 cm$^{-1}$

NMR (DMSO-d$_6$, δ): 1.37 (9H, s), 1.83, (3H, s), 3.21–3.27 (2H, m), 4.18–4.28 (1H, m), 6.75–6.85 (1H, m), 7.99 (1H, d, J=7.9 Hz)

MASS (m/z): 245 (M−H)$^-$

Preparation 17

To a mixture of N-(t-butoxycarbonyl)-2(S)-acetylamino-β-alanine (3.0 g) in dimethylformamide (60 ml) was added NaHCO$_3$ (2.05 g) at −2° C., and a solution of benzyl bromide in dimethylformamide (60 ml) was added by using a dropping funnel under stirring. The mixture was stirred overnight around 26° C., then poured into a mixture of ice-water (300 ml) and hexane-ethyl acetate (8:2, 500 ml). After the organic layer was separated, the aqueous layer was extracted again with hexane-ethyl acetate (8:2, 300 ml). The combined organic layer was washed with water (300 ml×2), brine (300 ml) and dried over Na$_2$SO$_4$, and evaporated in vacuo. The residue was purified by silica gel chromatography eluting with hexane-ethyl acetate (8:2) to give N-(t-butoxycarbonyl)-2(S)-acetylamino-β-alanine benzyl ester (3.68 g).

IR (KBr): 3361, 3324, 1739, 1687, 1650, 1536, 1456, 1440, 1392, 1369, 1346, 1319, 1278, 1251, 1203, 1174 cm$^{-1}$

NMR (CDCl$_3$, δ): 1.42 (9H, s), 2.03 (3H, s), 3.51–3.56 (2H, m), 4.60–4.68 (1H, m), 4.80 (1H, br), 5.18 (2H, s), 7.36 (5H, singlet like)

MASS (m/z): 237 (M−Boc+2H)$^+$

Preparation 18

To an ice-cooled solution of N-(t-butoxycarbonyl)-2(S)-acetylamino-β-alanine benzyl ester (3.44 g) in ethyl acetate (35 ml) was added 4N HCl in ethyl acetate (25.5 ml). The mixture was stirred for 2.5 hours at an ambient temperature, then the solvent was decanted. The residue was washed with diethyl ether several times, and dried in vacuo to give 2(S)-acetylamino-β-alanine benzyl ester hydrochloride (2.31 g) as a white powder.

IR (KBr): 3413, 3245, 1739, 1660, 1612, 1537, 1500, 1454, 1377, 1307, 1220, 1166 cm$^{-1}$

NMR (DMSO-d$_6$, δ) 1.89 (3H, s), 3.03–3.28 (2H, m), 4.54–4.65 (1H, m), 5.15 (2H, s), 7.33–7.39 (5H, m), 8.25 (3H, br), 8.67 (1H, d, J=7.7 Hz)

MASS (m/z): 237 (M+H)$^+$

Preparation 19

To a solution of 2(S)-acetylamino-β-alanine benzyl ester hydrochloride (1.86 g), N-(t-butoxycarbonyl)-3(R)-nipecotic acid (1.64 g) and 1-hydroxybenzotriazole (0.97 g) in dimethylformamide (25 ml) was added 1-ethyl-3-(3-dimethylaminopropyl)carbodiimide (1.31 ml) at 0° C. The mixture was stirred for 2 hours at room temperature, then poured into ice water-ethyl acetate. The separated organic layer was washed with water, aqueous saturated NaHCO$_3$, brine, dried over Na$_2$SO$_4$, and evaporated in vacuo. The residue was purified by silica gel chromatography eluting with CHCl$_3$—MeOH (95:5) to give N-[(R)-1-(t-butoxycarbonyl)-3-piperidyl-carbonyl]-2(S)-acetylamino-β-alanine benzyl ester (2.84 g).

IR (Film): 3300, 2938, 1741, 1666, 1648, 1552, 1533, 1469, 1434, 1367, 1301, 1265, 1241, 1151 cm$^{-1}$ NMR (CDCl$_3$, δ): 1.46 (9H, S), 1.55–1.77 (4H, m), 2.04 (3H, s), 2.10–2.22 (1H, br), 3.10 (2H, br), 3.79 (2H, br), 3.64–3.67 (2H, m), 3.79–3.85 (1H, br), 4.62–4.71 (1H, m), 5.18 and 5.30 (total 2H, s), 7.26–7.40 (5H, m)

MASS (m/z): 348 (M−Boc+2H)$^+$

Preparation 20

To an ice-cooled solution of N-[(R)-1-(t-butoxycarbonyl)-3-piperidylcarbonyl]-2 (S)-acetylamino-β-alanine benzyl ester (2.7 g) was added 4N HCl in ethyl acetate (25.5 ml). The mixture was stirred for 2.5 hours at an ambient temperature, then the solvent was decanted. The residue was washed with diethyl ether several times, and dried in vacuo to give N-[(R)-3-piperidylcarbonyl]-2(S)-acetylamino-β-alanine benzyl ester hydrochloride (2.29 g) as a white powder.

IR (Film): 3267, 3064, 2958, 1741, 1656, 1543, 1452, 1376 cm$^{-1}$

NMR (DMSO-d$_6$, δ): 1.45–1.87 (4H, m), 1.91 (3H, s), 2.62–2.85 (3H, m), 3.09–3.46 (4H, m), 4.38–4.42 (1H, m), 5.01–5.14 (2H, m), 7.37–7.39 (5H, m), 8.37–8.41 (2H, m), 8.78 (1H, br), 8.98 (1H, br)

MASS (m/z): 348 (M+H)$^+$

EXAMPLE 1

A mixture of N-[(R)-1-[3-(1-tert-butoxycarbonyl-4-piperidyl)propionyl]-3-piperidylcarbonyl]-2(S)-benzyloxycarbonylamino-β-alanine methyl ester (20 g) and 10% Pd on carbon (50% wet) (5 g) in methanol (500 ml) was stirred vigorously under a hydrogen atmosphere (1 atm) at room temperature. After 2 hours, the insolved material was removed by filtration, and the filtrate was concentrated in vacuo. The residue was dissolved in tetrahydrofuran (200 ml), and cooled to 0° C. 1N aqueous LiOH (116 ml) solution was added to the solution within 15 minutes at 0–3° C. After the mixture was stirred for 45 minutes at 0° C., acetic anhydride (6.89 ml) was added to the mixture within 15 minutes at 0–4° C. The mixture was stirred for 30 minutes at 0° C., then diethyl ether (150 ml) was added. The aqueous layer was separated, and the pH of it was adjusted to 2.5 with aqueous 20% KHSO$_4$, then extracted with ethyl acetate. The extract was dried over Na$_2$SO$_4$, and concentrated in vacuo to give N-[(R)-1-[3-(1-tert-butoxycarbonyl-4-piperidyl)propionyl]-3-piperidylcarbonyl]-2(S)-acetylamino-β-alanine (16.3 g) as a colorless oil.

IR (KBr): 3303, 2931, 1732, 1664, 1544, 1475, 1436 cm$^{-1}$

NMR (CDCl$_3$, δ) 1.07–1.25 (2H, m), 1.44 (9H, s), 1.51–1.76 (7H, m), 1.89–1.95 (2H, m), 2.05 (3H, s), 2.35–2.39 (3H, m), 2.61–2.73 (2H, m), 3.24–3.35 (2H, m), 3.56–3.84 (3H, m), 4.06–4.20 (3H, m), 4.33–4.60 (1H, m), 7.43–7.51 (2H, m)

MASS (m/z): 519 (M+Na)$^+$

EXAMPLE 2

N-[(S)-1-[3-(1-tert-Butoxycarbonyl-4-piperidyl)propionyl]-3-piperidylcarbonyl]-2(S)-acetylamino-β-alanine was obtained from N-[(S)-1-[3-(1-tert-Butoxycarbonyl-4-piperidyl)propionyl]-3-piperidylcarbonyl]-2 (S)-benzyloxycarbonylamino-β-alanine methyl ester according to a similar manner to that of Example 1.

IR (KBr): 3311, 1738, 1678, 1668, 1655 cm$^{-1}$

NMR (CDCl$_3$, δ): 1.00–2.11 (11H, m), 1.45 (9H, s), 2.03 (3H, s), 2.33–2.40 (3H, m), 2.60–2.73 (2H, m), 3.06–3.26 (2H, m), 3.48–4.59 (9H, m), 7.52–7.58 (1H, m), 7.70 (1H, d, J=7.0 Hz)

MASS (m/z): 497 (M$^+$+1)

EXAMPLE 3

N-[(S)-1-[3-(1-tert-Butoxycarbonyl-4-piperidyl)propionyl]-3-piperidylcarbonyl]-2(R)-acetylamino-β-alanine was obtained from N-[(S)-1-[3-(1-tert-Butoxycarbonyl-4-piperidyl)propionyl]-3-piperidylcarbonyl]-2(R)-benzyloxycarbonylamino-β-alanine methyl ester according to a similar manner to that of Example 1.

IR (KBr): 3311, 1738, 1720, 1676, 1668, 1655 cm$^{-1}$

NMR (CDCl$_3$, δ): 1.01–2.06 (11H, m), 1.45 (9H, s), 2.06 (3H, s), 2.12–2.40 (3H, m), 2.61–2.73 (2H, m), 3.09–3.86 (6H, m), 4.00–4.64 (3H, m), 7.39–7.43 (1H, m)

MASS (m/z): 497 (M$^+$+1)

EXAMPLE 4

N-[(R)-1-[3-(1-tert-Butoxycarbonyl-4-piperidyl)-propionyl]-3-piperidylcarbonyl]-2(S)-acetylamino-β-alanine was obtained from N-[(R)-1-[3-(1-tert-Butoxycarbonyl-4-piperidyl)propionyl]-3-piperidylcarbonyl]-2(S)-benzyloxycarbonylamino-β-alanine ethyl ester according to a similar manner to that of Example 1, and was the same compound obtained in Example 1.

EXAMPLE 5

N-[(R)-1-[3-(1-tert-Butoxycarbonyl-4-piperidyl)propionyl]-3-piperidylcarbonyl]-2(R)-acetylamino-β-alanine was obtained from N-[(R)-1-[3-(1-tert-Butoxycarbonyl-4-piperidyl)propionyl]-3-piperidylcarbonyl]-2(R)-benzyloxycarbonylamino-β-alanine methyl ester according to a similar manner to that of Example 1.

IR (KBr): 3305.4, 2975.6, 2933.2, 2861.8, 1733.7, 1660.4, 1544.7 cm$^{-1}$

NMR (DMSO-d$_6$, δ): 0.90–1.95 (11H, m), 1.38 (9H, s), 1.84 (3H, s), 2.20–2.80 (5H, m), 2.80–3.60 (4H, m), 3.70–4.00 (3H, m), 4.20–4.45 (2H, m), 7.90–8.10 (2H, m)

MASS (m/z): 495 (M−H)$^-$

EXAMPLE 6

N-[(R)-1-[3-(1-tert-Butoxycarbonyl-4-piperidyl)propionyl]-3-piperidylcarbonyl]-2(R)-acetylamino-β-alanine was obtained from N-[(R)-1-[3-(1-tert-Butoxycarbonyl-4-piperidyl)propionyl]-3-piperidylcarbonyl]-2(R)-benzyloxycarbonylamino-β-alanine ethyl ester according to a similar manner to that of Example 1, and was the same compound obtained in Example 5.

EXAMPLE 7

A mixture of N-[(R)-1-[3-(1-tert-butoxycarbonyl-4-piperidyl)propionyl]-3-piperidylcarbonyl]-2(S)-benzyloxycarbonylamino-β-alanine benzyl ester (540 ml), acetic acid (0.046 ml) and 10% Pd—C (108 mg) in methanol (11 ml) was hydrogenated at atmospheric pressure for 1.5 hours. After the catalyst was removed by filtration, the filtrate was concentrated in vacuo. The residue was resolved in a mixture of dioxane (4.8 ml) and 1N aqueous NaOH (2.46 ml), cooled down to 0° C., and added acetic anhydride (0.12 ml) in dropwise. After 5 minutes, the temperature was allowed to reach to room temperature. Water and ethyl acetate were poured into the reaction mixture, and the separated aqueous layer was adjusted to pH 3.0 with aqueous 5% KHSO$_4$, extracted with ethyl acetate three times. The combined organic layer was washed with brine, dried over Na$_2$SO$_4$ and evaporated in vacuo to give N-[(R)-1-[3-(1-tert-butoxycarbonyl-4-piperidyl)propionyl]-3-piperidylcarbonyl]-2(S)-acetylamino-β-alanine (332 mg), which was the same compound obtained in Example 1.

EXAMPLE 8

To a solution of N-[(R)-1-[3-(1-tert-butoxycarbonyl-4-piperidyl)propionyl]-3-piperidylcarbonyl]-2(S)-acetylamino-β-alanine (14.9 g) in ethyl acetate (150 ml) was added dropwise 4N HCl in ethyl acetate (74.8 ml) for 10 minutes at 0° C. After the mixture was stirred for 1 hour and 20 minutes, a white solid was collected by filtration, and dried in vacuo. The powder was dissolved in water (150 ml), and the solution was neutralized to pH 6.5 with saturated aqueous NaHCO$_3$. The solution was concentrated to about 100 ml, then applied to ODS column (Disogel-120SP®, 1 l), and eluted with 4–6% CH$_3$CN/water. The eluent was concentrated in vacuo, and the residue was dissolved 0.5% aqueous ethanol (200 ml). After the mixture was stirred at room temperature overnight, the resultant solid was collected by filtration, and dried in vacuo to give N-[(R)-1-[3-(4-piperidyl)propionyl]-3-piperidylcarbonyl]-2-(S)-acetylamino-β-alanine (6.85 g) as a white crystal.

IR (KBr): 3430, 2942, 2861, 1630, 1610, 1475, 1444, 1394 cm$^{-1}$

NMR (D$_2$O, δ): 1.37–1.94 (11H, m), 2.03 (3H, s), 2.35–2.54 (3H, m), 2.85–3.06 (3H, m), 3.21–3.47 (4H, m), 3.63–3.74 (1H, m), 3.89–3.92 (1H, m), 4.15–4.31 (1H, m), 4.35–4.41 (1H, m)

MASS (m/z): 397 (M$^+$+1)

mp: 233° C.

$[α]_D^{26}$: −11.8° (c=1.0, MeOH)

Anal Calcd. for C$_{19}$H$_{32}$N$_4$O$_5$.2H$_2$O: C 52.76, H 8.39, N 12.95 Found C 52.42, H 8.92, N 12.84

EXAMPLE 9

N-[(S)-1-[3-(4-Piperidyl)propionyl]-3-piperidylcarbonyl]-2(S)-acetylamino-β-alanine was obtained from N-[(S)-1-[3-(1-tert-Butoxycarbonyl-4-piperidyl)propionyl]-3-piperidylcarbonyl]-2(S)-acetylamino-β-alanine according to a similar manner to that of Example 8.

IR (KBr): 2947, 2858, 1666, 1628, 1599 cm$^{-1}$

NMR (D$_2$O, δ): 1.30–2.30 (11H, m), 2.03 (3H, s), 2.35–2.55 (3H, m), 2.81–3.05 (3H, m), 3.12–3.52 (4H, m), 3.60–3.70 (1H, m), 3.85–3.97 (1H, m), 4.13–4.30 (1H, m), 4.35–4.42 (1H, m)

MASS (m/z): 397 (M$^+$+1)

mp: 131.2–131.7° C.

$[α]_D^{27}$: +46.2° (c=1.0, MeOH)

Anal Calcd. for C$_{19}$H$_{32}$N$_4$O$_5$.2.5H$_2$O: C 51.69, H 8.45, N 12.69 Found: C 51.25, H 8.64, N 12.53

EXAMPLE 10

N-[(S)-1-[3-(4-Piperidyl)propionyl]-3-piperidylcarbonyl]-2(R)-acetylamino-β-alanine was obtained from N-[(S)-1-[3-(1-tert-Butoxycarbonyl-4-piperidyl)propionyl]-3-piperidylcarbonyl]-2(R)-acetylamino-β-alanine according to a similar manner to that of Example 8.

IR (KBr): 3421, 2941, 2860, 1645, 1637, 1630, 1618 cm$^{-1}$

NMR (D$_2$O, δ): 1.37–1.95 (11H, m), 2.03 (3H, s), 2.36–2.54 (3H, m), 2.80–3.01 (3H, m), 3.17–3.48 (4H, m), 3.63–3.75 (1H, m), 3.81–3.95 (1H, m), 4.16–4.32 (1H, m), 4.34–4.41 (1H, m)

MASS (m/z): 397 (M$^+$+1)

mp: >220° C.

$[α]_D^{26}$: +12.2° (c=1.0, MeOH)

Anal Calcd. for C$_{19}$H$_{32}$N$_4$O$_5$.2H$_2$O: C 52.76, H 8.39, N 12.95 Found: C 52.87, H 8.99, N 12.90

EXAMPLE 11

N-[(R)-1-[3-(4-Piperidyl)propionyl]-3-piperidylcarbonyl]-2(R)-acetylamino-β-alanine was obtained from N-[(R)-1-[3-(1-tert-Butoxycarbonyl-4-piperidyl)propionyl]-3-piperidylcarbonyl]-2(R)-acetylamino-β-alanine according to a similar manner to that of Example 8.

IR (KBr): 3463.5, 3251.4, 3089.4, 1666.2, 1627.6, 1598.7, 1542.8 cm$^{-1}$

NMR (D$_2$O, δ): 1.30–2.10 (11H, m), 2.03 (3H, s), 2.30–2.65 (3H, m), 2.80–3.70 (8H, m), 3.80–4.45 (3H, m)

MASS (m/z): 397 (M+H)$^+$, 419 (M+Na)$^+$ mp: 124.0–124.5° C. (10% Isopropanol aq.)

$[α]_D^{29}$: 45.9° (c=1.0, MeOH)

Anal Calcd. for C$_{19}$H$_{32}$N$_4$O$_5$.3H$_2$O: C 50.65, H 8.50, N 12.44 Found: C 50.88, H 8.57, N 12.49

EXAMPLE 12

To a solution of N-[(R)-3-piperidylcarbonyl]-2(S)-acetylamino-β-alanine benzyl ester hydrochloride (231 mg), 3-(4-pyridyl)-2-propenoic acid (82 mg) and 1-hydroxybenzotriazole (81 mg) in dimethylformamide (2 ml) was added 1-ethyl-3-(3-dimethylaminopropyl) carbodiimide (0.11 ml) at 0° C. The mixture was stirred for 2 hours at room temperature, then poured into ice water-ethyl acetate. The separated organic layer was washed with water, aqueous saturated NaHCO$_3$, brine, dried over Na$_2$SO$_4$, and evaporated in vacuo. The residue was purified by silica gel chromatography eluting with CHCl$_3$—MeOH (96:4) to give N-[(R)-1-[3-(4-pyridyl)-2-propenoyl]-3-piperidylcarbonyl]-2(S)-acetylamino-β-alanine benzyl ester (263 mg) as a colorless oil.

IR (Film): 3376, 3334, 2937, 1739, 1650, 1599, 1550, 1455, 1394, 1301, 1224 cm$^{-1}$ NMR (CDCl$_3$, δ): 1.58–1.87 (4H, m), 2.02 and 2.06 (total 3H, s), 2.15–2.25 (1H, m), 2.40–2.50 (1H, m), 3.43–3.76 (4H, m), 3.91–4.00 (2H, m), 4.70–4.78 (1H, m), 5.05–5.19 (2H, m), 7.08 (1H, d, J=15.6 Hz), 7.32–7.38 (7H, m), 7.54 (1H, d, J=15.6 Hz), 8.62–8.65 (2H, m)

MASS (m/z): 479 (M+H)$^+$

EXAMPLE 13

A mixture of N-[(R)-1-[3-(4-pyridyl)-2-propenoyl]-3-piperidylcarbonyl]-2(S)-acetylamino-β-alanine benzyl ester (233 mg), PtO$_2$ (60 mg) in ethanol (10 ml), 4N HCl in ethyl acetate (121 μl) and PtO$_2$ (50% wet, 1.2 g) was stirred vigorously under hydrogen (1 atm) atmosphere. After 3.5 hours, the catalyst was removed by filtration, and the filtrate was evaporated in vacuo. The residue was dissolved in water (10 ml). The solution was adjusted to pH 6.5 with aqueous NaHCO$_3$, then evaporated in vacuo. The residue was purified by ODS-chromatography (Disogel SP-120®) eluting with 4% CH₃CN/water. The eluent was concentrated in vacuo and freeze-dried to give N-[(R)-1-[3-(4-piperidyl)propionyl]-3-piperidylcarbonyl]-2(S)-acetylamino-β-alanine (154 mg) as a white powder, which is the compound obtained in Example 8.

Preparation 21

A mixture of 3-piperidinecarboxylic acid ethyl ester (50 g) and L-tartaric acid (48 g) in isopropyl alcohol (1000 ml) and water (5 ml) was stirred at 40° C. The solution was cooled and stirred at room temperature.

The precipitate was filtered, washed with isopropyl alcohol (50 ml) and dried in vacuo to give (R)-3-piperidinecarboxylic acid ethyl ester L-tartaric acid salt as white solid. The solid was resolved with isopropyl alcohol (726 ml) and water (36 ml) at 65° C. The solution was cooled and stirred at room temperature. The precipitate was filtered and dried to give pure (R)-3-piperidinecarboxylic acid ethyl ester L-tartaric acid salt (30.3 g).

To a solution of (R)-3-piperidinecarboxylic acid ethyl ester L-tartaric acid salt (30.3 g) in ethyl acetate (300 ml) and water (60 ml), 12% aqueous sodium hydroxide was added to adjust pH to 13. Aqueous layer was extracted with ethyl acetate (60 ml) two times and combined organic layer was dried with sodium sulfate (8 g). Organic layer was concentrated in vacuo to give (R)-3-piperidinecarboxylic acid ethyl ester (15.3 g).

IR. (oil): 2939, 2856, 1731, 1446, 1373 cm-1

NMR(DMSO-d₆, δ):1.66 (3H, t), 1.27–1.58 (3H, m), 1.81–1.89(1H, m), 2.26–2.41(2H, m), 2.46(1H, m), 2.57(1H, m), 2.66(1H, d), 2.98(1H, d), 4.03(2H, q)

MASS (m/z): 157

Preparation 22

To a mixture of malonic acid (12 g), pyridine (7.6 g) in ethanol(41 ml) was added dropwise 4-pyridinecarbaldehyde (10.3 g) at 40° C. The mixture was stirred at 80° C. for 5 hours, then cooled to room temperature. The precipitate was filtered washed with ethanol and dried in vacuo to give 3-(4-pyridyl)-2-propenoic acid (10.4 g)

IR(KBr): 3054, 2359, 1700, 1645, 1607,1555, 1415, 1341, 1311 cm⁻¹

NMR(DMSO-d₆, δ): 3.33(1H, s), 6.78(1H, d), 7.52(1H, d), 7.66(2H, d), 8.62(2H, d)

MASS (m/z): 150 (M+1)

Preparation 23

A mixture of 3-(4-pyridyl)-2-propenoic acid (10 g) , 10% Pd—C (1 g) in acetic acid (40 ml) was hydrogenated (3.0 kg/cm²) at 65° C. for 8 hours. After the catalyst was removed by filtration, the filtrate was concentrated in vacuo. The residue was resolved in toluene (30 ml) and concentrated in vacuo. The residue was resolved in water (30 ml) and tetrahydrofuran (50 ml), cooled to 0° C., and triethylamine (33 g) was added dropwise at 5° C. Di-t-butyl dicarbonate (18.3 g) was added to the mixture at 20° C. and stirred overnight. PH was adjusted to 7 with HCl, organic layer was washed with 10% aqueous citric acid (40 ml), 5% aqueous sodium chloride (40 ml), dried over magnesium sulfate (5 g) and concentrated in vacuo. The residue was resolved in toluene (20 ml), concentrated in vacuo to 25 ml. The mixture was stirred at 40° C. for 3 hours, n-heptane (20 ml) was added to the mixture and stirred at 0° C. overnight. The precipitate was separated and dried to give 3-(1-tert-butoxycarbonyl-4-piperidyl)propionic acid as white solid (12.8 g).

IR(KBr): 3300, 2937, 1734, 1670, 1479, 1455, 1285, 1173 cm⁻¹

NMR(DMSO-d₆, δ) 0.9–1.0(2H, m), 1.38(9H, s), 1.3–1.5 (1H, m), 1.6(2H, m), 2.22(2H, t), 2.64(2H, m), 3.30(1H, s), 3.9(2H, m)

MASS(m/z): 158(M+1−BOC)

Preparation 24

To a mixture of (R)-3-piperidinecarboxylic acid ethyl ester (7.7 g), 3-(1-tert-butoxycarbonyl-4-piperidyl)propionic acid (12.5 g), 1-hydroxybenztriazole (6.6 g) in dimethylformamide was added 1-ethyl-3-(3-dimethylaminopropyl)carbodiimide (7.6 g) at 5° C. The mixture was stirred at 25° C. overnight. Ethyl acetate (96 ml) and water (94 ml) was added to the mixture. Organic layer was separated and aqueous layer was extracted with ethyl acetate (94 ml) two times. Combined organic layer was washed with 9% aqueous sodium bicarbonate (63 ml), water (63 ml), 20% aqueous sodium chloride (63 ml) and concentrated in vacuo.

The residue was resolved in methanol (164 ml) and was added to the solution of lithium hydroxide (3.9 g) in water (110 ml) at 5° C. The mixture was stirred overnight, then pH was adjusted to 2.6 with 3N-hydrochloric acid and stirred overnight at 35° C.

After cooling to 0° C., the precipitate was filtered, washed with 30% aqueous methanol and dried in vacuo to give (R)-1-[3-(1-tert-butoxycarbonyl-4-piperidyl)propionyl]-3-piperidinecarboxylic acid (13.8 g) as white solid.

IR(KBr): 2931, 2885, 1732, 1688, 1628, 1607, 1471, 1236, 1166 cm⁻¹

NMR(DMSO-d₆, δ): 0.92–1.06(2H, m), 1.28–1.51(3H, m), 1.38(9H, s), 1.51–1.78(4H, m), 1.8–2.0(1H, m), 2.2–2.4 (4H, m), 2.5–2.7(2H, m), 2.9–3.1(1H, m), 3.2–3.8(1H, m), 3.7–4.5(4H, m)

MASS(m/z): 269(M+1−BOC)

EXAMPLE 14

N-[(R)-1-[3-(1-tert-butoxycarbonyl-4-piperidyl)propionyl]-3-piperidylcarbonyl]-2(S)-acetylamino-β-alanine (20.0 g) was treated under atmosphere RH 50%, 25° C. for 40 hours to give N-[(R)-1-[3-(4-piperidyl)propionyl]-3-piperidylcarbonyl]-2(S)-acetylamino-β-alanine trihydrate (21.6 g), whose stability against humidity was very good.

IR(KBr): 2726, 2606, 1658, 1616, 1539, 1328, 1304, 1268, 1232, 1223 cm⁻¹

X-Ray powder diffraction: (2 θ) 11.26, 13.39, 18.60, 20.43, 21,16, 22.05

What is claimed is:

1. The compound N-[(R)-1-[3-(4-piperidyl)propionyl]-3-piperidyl-carbonyl]-2(S)-acetylamino-β-alanine trihydrate or a trihydrate salt thereof.

2. The N-[(R)-1-[3-(4-piperidyl)propionyl]-3-piperidyl-carbonyl]-2(S)-acetylamino-β-alanine trihydrate of claim 1, which has the following structure:

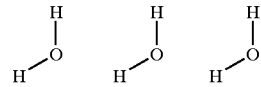

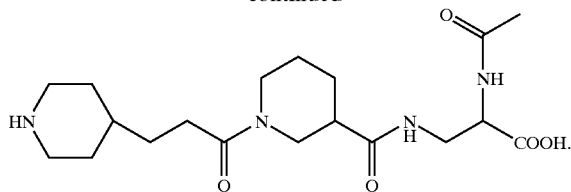

3. The compound of claim 1 in the form of a salt.

4. The compound of claim 1 in the form of a metal salt.

5. The compound of claim 1 in the form of an alkaline earth metal salt.

6. The compound of claim 1 in the form of an ammonium or organic base salt.

7. The compound of claim 1 in the form of an organic acid addition salt.

8. The compound of claim 1 in the form of a salt with an amino acid.

9. A stereoisomer of the compound of claim 1.

10. A composition comprising the compound of claim 1 and a pharmaceutically acceptable carrier.

11. A method for antagonizing glycoprotein IIb/IIIa activity comprising administering an effective amount of the compound of claim 1 to a subject in need thereof.

12. A method for inhibiting platelet aggregation comprising administering an effective amount of the compound of claim 1 to a subject in need thereof.

13. A method for inhibiting the binding of fibrinogen to blood platelets comprising administering an effective amount of the compound of claim 1 to a subject in need thereof.

* * * * *